United States Patent [19]

Fuchs et al.

[11] Patent Number: 4,529,557
[45] Date of Patent: Jul. 16, 1985

[54] COMBATING PESTS WITH NOVEL SUBSTITUTED PHENYLCYCLOPROPANECARBOXYLIC ACID ESTERS

[75] Inventors: Rainer Fuchs, Wuppertal; Erich Klauke, Odenthal-Hahnenberg; Ingeborg Hammann, Cologne; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 395,766

[22] Filed: Jul. 6, 1982

[30] Foreign Application Priority Data

Jul. 18, 1981 [DE] Fed. Rep. of Germany ....... 3128444

[51] Int. Cl.³ .................. C07C 121/50; C07C 149/40; C07C 69/76
[52] U.S. Cl. ................................ 260/465 D; 560/18; 560/59
[58] Field of Search ................ 260/465 D; 560/18, 59

[56] References Cited

U.S. PATENT DOCUMENTS 4,220,591 9/1980 Holan et al. ................ 260/465 D X
4,360,690 11/1982 Fuchs et al. ........................ 560/57

FOREIGN PATENT DOCUMENTS 0017952 10/1980 European Pat. Off.
0019787 12/1980 European Pat. Off.
0043492 1/1982 European Pat. Off.
2855422 7/1979 Fed. Rep. of Germany.
2837524 3/1980 Fed. Rep. of Germany.
2949342 6/1980 Fed. Rep. of Germany.

Primary Examiner—Delbert R. Phillips
Attorney, Agent, or Firm—Sprung Horn Kramer & Woods

[57] ABSTRACT

Substituted phenyl-cyclopropanecarboxylic acid esters of the formula

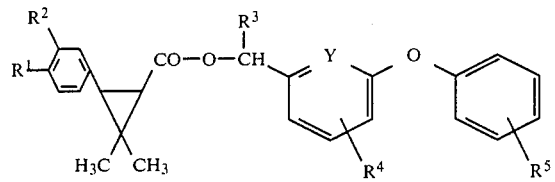

in which
$R^1$ represents an alkoxy or alkylthio radical which is monosubstituted or polysubstituted by identical or different halogen substituents,
$R^2$ represents a hydrogen or halogen atom, or
$R^1$ and $R^2$ together represent an alkylenedioxy radical which is monosubstituted or polysubstituted by identical or different halogen substituents,
$R^3$ represents a hydrogen atom, a cyano group or an alkyl, alkenyl or alkinyl radicals which is optionally monosubstituted or polysubstituted by identical or different halogen substituents,
Y represents a nitrogen atom or a methinyl radical, and
$R^4$ and $R^5$ are identical or different and represent a hydrogen or halogen atom, which possess pesticidal properties, plus novel intermediates therefor.

8 Claims, No Drawings

COMBATING PESTS WITH NOVEL SUBSTITUTED PHENYLCYCLOPROPANECARBOXYLIC ACID ESTERS

The invention relates to certain new substituted phenylcyclopropanecarboxylic acid esters, to a process for their production, and to their use as agents for combating pests. The invention further relates to certain new intermediate products for the foregoing process, and a process for the production of such intermediates.

It is known that certain phenyl-cyclopropanecarboxylic acid esters, such as α-cyano-3-phenoxybenzyl 3-(4-methoxyphenyl)-2,2-dimethyl-cyclopropanecarboxylate, are insecticides (see German Published Specification DOS No. 2,855,422).

The action of these compounds is however not always satisfactory, especially in the case of low active compound concentrations and use amounts.

The present invention now provides, as new compounds, the substituted phenyl-cyclopropanecarboxylic acid esters of the general formula

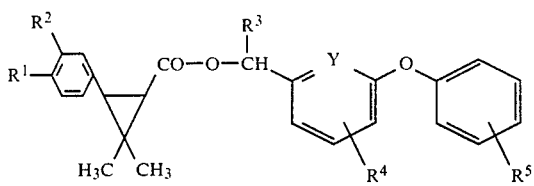

in which
$R^1$ represents an alkoxy or alkylthio radical which is monosubstituted or polysubstituted by identical or different halogen substituents,
$R^2$ represents a hydrogen or halogen atom, or $R^1$ and $R^2$ together represent an alkylenedioxy radical which is mono-substituted or polysubstituted by identical or different halogen substituents,
$R^3$ represents a hydrogen atom, a cyano, group or an alkyl, alkenyl or alkinyl radicals which is optionally monosubstituted or polysubstituted by identical or different halogen substituents,
Y represents a nitrogen atom or a methinyl radical and
$R^4$ and $R^5$ are identical or different and represent a hydrogen or halogen atom.

According to the present invention we further provide a process for the production of a compound of formula (I) of the present invention, characterized in that (a) a substituted 2,2-dimethyl-3-phenyl-cyclopropanecarboxylic acid of the general formula

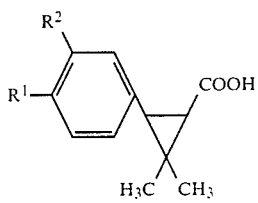

in which $R^1$ and $R^2$ have the meanings given above, or a reactive derivative thereof,
is reacted with a 3-phenoxy-benzyl alcohol or a phenoxypyridyl alcohol of the general formula

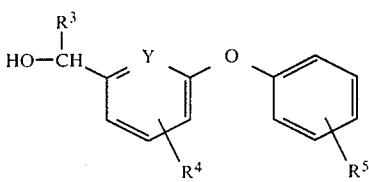

in which $R^3$, $R^4$, $R^5$ and Y have the meanings given above, or with a reactive derivative thereof, if appropriate in the presence of an acid-binding agent and/or of a catalyst, and if appropriate using one or more diluents, or (b) if a compound of the formula (I) in which $R^3$ represents a cyano group is required, a carboxylic acid chloride of the general formula

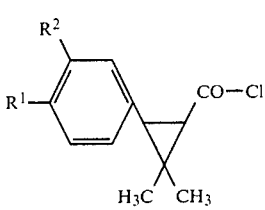

in which $R^1$ and $R^2$ have the meanings given above, is reacted with 3-phenoxy-benzaldehyde or 6-phenoxypyridine-2-carbaldehyde of the general formula

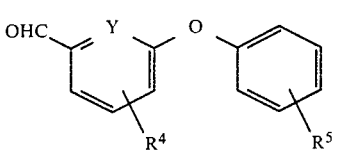

in which $R^4$, $R^5$ and Y have the meanings given above, and at least an equimolar amount of a water-soluble cyanide (preferably sodium cyanide or potassium cyanide), if appropriate in the presence of a catalyst and using a diluent.

The present invention further provides, as new intermediate compounds, the substituted 2,2-dimethyl-3-phenyl-cyclopropanecarboxylic acids of the general formula

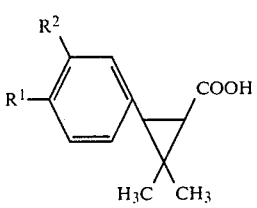

in which
$R^1$ represents a $C_1$ to $C_4$ alkoxy or $C_1$ to $C_4$ alkylthio radical which is monosubstituted or polysubstituted by identical or different halogen substituents,
$R^2$ represents a hydrogen or halogen atom, or
$R^1$ and $R^2$ together represent an alkylenedioxy radical which is monosubstituted or polysubstituted by identical or different halogen substituents.

According to the present invention we also provide a process for the production of a compound of the formula (II), characterized in that a substituted 2,2-dimethyl-3-phenylcyclopropanecarboxylic acid ester of the general formula

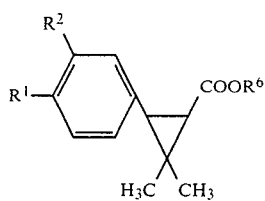

in which
R¹ and R² have the meanings given above and
R⁶ represents a C₁ to C₄ alkyl group,
is heated with an alkali metal hydroxide in the presence of a diluents, to a temperature between 50° and 200° C., and the mixture is then acidified at room temperature with a mineral acid.

The present invention also provides, as further new intermediate compounds, the substituted 2,2-dimethyl-3-phenyl-cyclopropanecarboxylic acid esters of the general formula

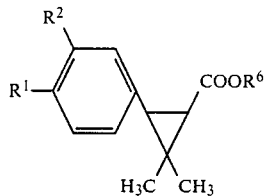

in which
R¹ represents an alkoxy or alkylthio radical which is monosubstituted or polysubstituted by identical or different halogen substituents,
R² represents a hydrogen or halogen atom, or
R¹ and R² together represent an alkylenedioxy radical which is monosubstituted or polysubstituted by identical or different halogen substituents, and
R⁶ represents a C₁ to C₄ alkyl radical.

According to the present invention we also provide a process for the production of a compound of the formula (IV), characterized in that a substituted 2-methyl-3-phenyl-propene of the general formula

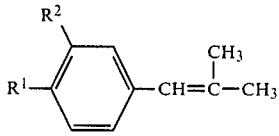

in which R¹ and R² have the meanings given above, is reacted with a diazoacetic acid ester of the general formula

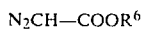

in which R⁶ has the meaning given above,
in the presence of a catalyst, at a temperature between 50° and 200° C.

The present invention also provides, as further new intermediate compounds, substituted 2-methyl-3-phenylpropenes of the general formula

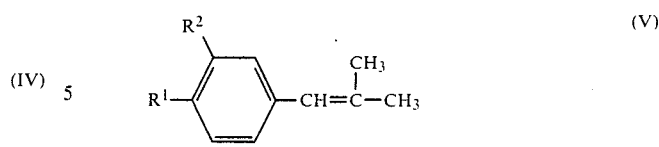

in which
R¹ represents an alkoxy or alkylthio radicals which is monosubstituted or polysubstituted by identical or different halogen substituents,
R² represents a hydrogen or hydrogen atom, or
R¹ and R² together represent an alkylenedioxy radical which is monosubstituted or polysubstituted by identical or different halogen substituents.

According to the present invention we further provide a process for the production of a compound of the formula (V), characterized in that a substituted benzaldehyde of the general formula

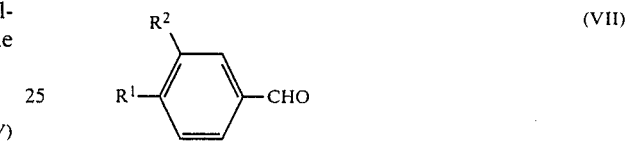

in which R¹ and R² have the meanings given above, is reacted with triphenyl-isopropyl-phosphorane of the formula

if appropriate using a diluent, at a temperature between −70° and +50° C.

The present invention also provides, as yet further new intermediate compounds, substituted benzaldehydes of the general formula

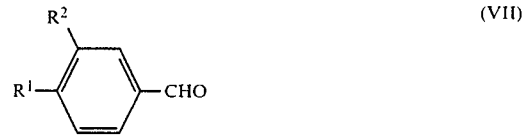

in which
R¹ represents an alkoxy or alkylthio radical which is monosubstituted or polysubstituted by identical or different halogen substituents, and
R² represents a halogen atom.

According to the present invention we further provide a process for the production of a compound of the formula (VII), characterized in that a substituted benzene of the general formula

in which
R¹ and R² have the meanings given above, and $R^7$ represents a hydroxymethyl radical, is converted into the corresponding aldehydes.

The new active compounds of the formula (I) are distinguished by a high insecticidal and acaricidal activity.

Surprisingly, the compounds according to the present invention, of the formula (I), show a considerably higher insecticidal and acaricidal activity than compounds known from the state of the art and of analogous constitution and identical direction of action.

The general formula (I) includes the various possible stereoisomers and optically active isomers, as well as their mixtures.

Preferred phenyl-cyclopropanecarboxylic acid esters of the formula of the present invention are those in which $R^1$ represents a $C_1$ or $C_2$ fluoroalkoxy, $C_1$ or $C_2$ chlorofluoroalkoxy $C_1$ or $C_2$ fluoroalkylthio or $C_1$ or $C_2$ chlorofluoroalkylthio radical, $R^2$ represents a hydrogen, chlorine or bromine atom, or $R^1$ and $R^2$ together represent a $C_1$ or $C_2$ fluoroalkylenedioxy radical, $R^3$ represents a hydrogen atom or a cyano, $C_1$ to $C_4$ alkyl, $C_2$ to $C_4$ alkenyl or $C_2$ to $C_4$ alkinyl radical, $R^4$ and $R^5$ are identical or different and represent a hydrogen, fluorine, chlorine or bromine atom, and Y represents a nitrogen atom or a methinyl radical.

Very particularly preferred substituted phenylcyclopropanecarboxylic acid ester of the formula (I) of the present invention are those in which $R^1$ represents a chlorotrifluoroethoxy, tetrafluoroethoxy, chlorodifluoromethoxy, trifluoromethoxy, trifluoromethylthio or difluoromethoxy radical, $R^2$ represents a hydrogen, chlorine or bromine atom, or $R^1$ and $R^2$ together represent a trifluoroethylenedioxy or difluoromethylenedioxy radical, $R^3$ represents a hydrogen atom or a cyano group, $R^4$ represents a hydrogen atom, 4-fluoro, 4-chloro or 4-bromo, $R^5$ represents a hydrogen atom, and Y represents a nitrogen atom or a methinyl radical.

The following compounds of the formula (I) may be individually mentioned, in addition to the compounds mentioned in the preparative examples hereinbelow:

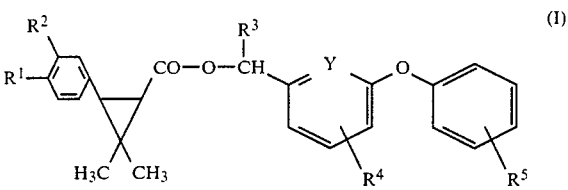

TABLE 1

| $R^1$ | $R^2$ | $R^3$ | $R^4$ | $R^5$ | Y |
|---|---|---|---|---|---|
| $F_3CS$ | H | CN | H | H | N |
| $F_3CO$ | Br | CN | H | H | N |
| $F_3CO$ | Cl | CN | H | H | CH |
| $F_3CO$ | Cl | H | H | H | CH |
| $F_3CO$ | Cl | H | 4-F | H | CH |
| $F_3CO$ | Cl | CN | 4-F | H | CH |
| $F_3CO$ | Cl | CN | H | H | N |
| $F_2HCO$ | Cl | CN | H | H | CN |
| $F_2HCO$ | Cl | H | H | H | CH |
| $F_2HCO$ | H | H | 4-F | H | CH |
| $F_2HCO$ | Cl | CN | 4-F | H | CH |
| $F_2HCO$ | H | CN | H | H | N |
| —O—CHF—CF$_2$—O— | | CN | H | H | CH |

TABLE 1-continued

| $R^1$ | $R^2$ | $R^3$ | $R^4$ | $R^5$ | Y |
|---|---|---|---|---|---|
| —O—CHF—CF$_2$—O— | | H | H | H | CH |
| —O—CHF—CF$_2$—O— | | CN | 4-F | H | CH |
| —O—CHF—CF$_2$—O— | | H | 4-F | H | CH |
| —O—CF$_2$—O— | | CN | H | H | CH |
| —O—CF$_2$—O— | | H | H | H | CH |
| —O—CF$_2$—O— | | CN | 4-F | H | CH |
| —O—CF$_2$—O— | | H | 4-F | H | CH |
| FClHC—CF$_2$O— | H | CN | H | H | CH |
| FClHC—CF$_2$O— | Cl | H | H | H | CH |
| FClHC—CF$_2$O | H | H | 4-F | H | CH |
| FClHC—CF$_2$O— | Cl | CN | 4-F | H | CH |
| F$_2$HC—CF$_2$O— | Cl | CN | H | H | CH |
| F$_2$HC—CF$_2$O— | H | H | H | H | CH |
| F$_2$HC—CF$_2$O— | Cl | H | 4-F | H | CH |
| F$_2$HC—CF$_2$O— | Cl | CN | 4-F | H | CH |

A preferred form of reaction variant (a) for the production of the new compounds of the formula (I) ("reaction variant (a')") is characterized in that a substituted 2,2-dimethyl-3-phenyl-cyclopropanecarboxylic acid chloride of the formula (IIa), as defined in reaction variant (b), as a reactive derivative of the substituted 2,2-dimethyl-3-phenyl-cyclopropanecarboxylic acid of the formula (II), is reacted with 3-phenoxy-benzyl alcohols or 6-phenoxy-pyrid-2-yl alcohols of the formula (III), as given above, in the presence of an acid-building agent and using a diluent.

If, for example, 3-(3-bromo-4-trifluoromethoxyphenyl)-cyclopropanecarboxylic acid chloride and 6-phenoxy-pyrid-2-yl-methanol or 6-phenoxy-pyridine-2-carbaldehyde and sodium cyanide are used as starting materials, reaction variant (a') and reaction variant (b) are illustrated by the following equations:

Reaction variant (a')

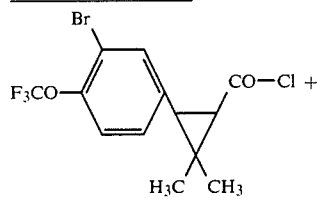

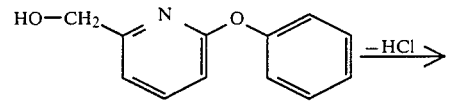

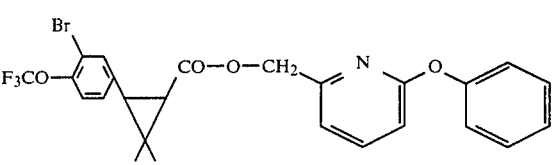

Reaction variant (b)

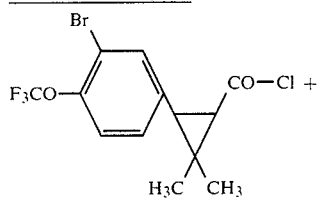

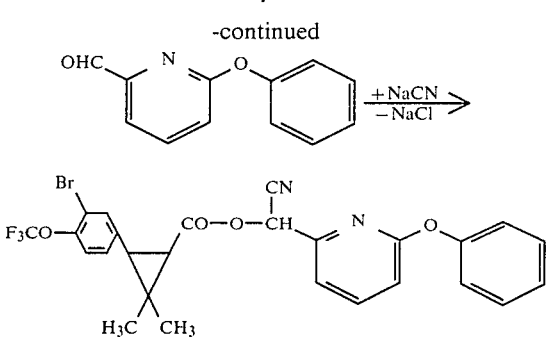

In general, reaction variants (a) and (b) are carried out using diluents.

Virtually any of the inert organic solvents are suitable diluents. These include, in particular, aliphatic and aromatic, optionally halogenated hydrocarbons (such as pentane, hexane, heptane, cyclohexane, petroleum ether, petrol, ligroin, benzene, toluene, xylene, methylene chloride, ethylene chloride, chloroform, carbon tetrachloride, chlorobenzene and o-dichlorobenzene), ethers (such as diethyl ether and dibutyl ether, glycol dimethyl ether and diglycol dimethyl ether, tetrahydrofuran and dioxane), ketones (such as acetone, methyl ethyl ketone, methyl isopropyl ketone and methyl isobutyl ketone), esters (such as methyl acetate and ethyl acetate), nitriles (such as acetonitrile and propionitrile), amides (such as dimethylformamide, dimethylacetamide and N-methyl-pyrrolidone), dimethylsulphoxide, tetramethylenesulphone and hexamethylphosphoric acid triamide.

Reaction variant (b) is preferably carried out using water as a second component, in addition to a hydrocarbon as a water-immiscible organic solvent, and if appropriate in the presence of a catalyst. Compounds which are suitable for transferring anions from water to organic solvents are used, if appropriate, as catalysts. Examples of these are benzyl-triethyl-ammonium bisulphate, tetrabutylammonium bromide and methyl-tricapryl-ammonium chloride ("Aliquat" 336).

Any of the customary acid-binding agents can be used in reaction variant (a). The following may be mentioned as examples: alkali metal hydroxides (such as sodium and potassium hydroxide), alkali metal carbonates, (such as sodium and potassium carbonate), alkali metal alcoholates (such as sodium and potassium methylate and ethylate) and aliphatic and aromatic and also heterocyclic amines (such as triethylamine and trimethylamine, N,N-dimethylaniline, N,N-dimethyl-benzylamine, pyridine, diazabicyclooctane, diazabicyclononane and diazabicycloundecene).

The reaction temperature is generally maintained between 0° and 100° C. reaction variants (a) and (b), and preferably between 10° and 50° C. in variants (a') and (b). The process is carried out in general under normal pressure.

In general, to carry out reaction variants (a) and (b), approximately equimolar amounts of the starting materials, if appropriate together with acid acceptors or catalysts, are combined, if appropriate, in suitable diluents, and the reaction mixtures are stirred for several hours. For working-up, which can be effected according to customary methods, the mixture is diluted, if appropriate, with water and/or a water-immiscible organic solvent, and the organic phase is separated off, washed with water, dried and filtered. The solvent is carefully distilled off under reduced pressure, the crude product remaining as the residue.

Preferred novel 2,2-dimethyl-3-phenyl-cyclopropanecarboxylic acids to be used as starting materials, and the corresponding acid-chlorides of formula (IIa) are those in which $R^1$ and $R^2$ have the same meanings as those given in the definition of these groups for the preferred and very particularly preferred compounds of formula (I).

The carboxylic acid-chlorides of the formula (IIa) may be obtained from the corresponding carboxylic acids of the formula (II) according to customary methods, for example by reaction with thionyl chloride, if appropriate using a diluent (such as carbon tetrachloride) at a temperature between 0° and 100° C., and subsequent distillation.

The following may be mentioned as examples of the compounds of the formula (II) or (IIa): 3-(3-bromo-4-trifluoromethoxy-phenyl)-, 3-(4-trifluoromethoxyphenyl)-, 3-(4-trifluoromethylthio-phenyl)-, 3-(3-chloro-4-trifluoromethoxy-phenyl)-, 3-(3,4-trifluoroethylenedioxy-phenyl)-, 3-(3,4-difluoromethylenedioxy-phenyl)-, 3-(3-chloro-4-(2-chloro-1,1,2-trifluoroethoxy)-phenyl)-, 3-(3-chloro-4-(1,1,2,2-tetrafluoroethoxy)-phenyl)-, 3-(3-chloro-4-chlorodifluoromethoxyphenyl)- and 3-(3-chloro-4-difluoromethoxy-phenyl)-2,2-dimethylcyclopropanecarboxylic acid and the corresponding acid-chlorides.

The new substituted 2,2-dimethyl-3-phenyl-cyclopropanecarboxylic acids of the formula (II) are obtained according to the process which forms a further subject of the present invention, described previously, by the reaction of a substituted 2,2-dimethyl-3-phenyl-cyclopropanecarboxylic acid ester of the formula (IV), as given above, with an alkali metal hydroxide (such as sodium or potassium hydroxide, in the presence of a diluents (such as water and/or alcohol, for example, ethanol) at a temperature between 50° and 100° C.

Working-up can be carried out according to customary methods, for example by extracting the mixture, after dilution with water, with a water-immiscible organic solvent, drying the organic phase and filtering it, and carefully distilling off the solvent under reduced pressure, the product being obtained as the residue.

The compounds of the formula (III) are known (see U.S. Pat. No. 4,163,787, U.S. Pat. No. 3,835,176 and U.S. Pat. No. 4,218,469.

Examples of preferred starting materials of the formula (III) are 4-fluoro-3-phenoxy-benzyl alcohol, 4-fluoro-3-phenoxy-benzaldehyde, 3-phenoxy-benzyl alcohol, 3-phenoxy-benzaldehyde, α-cyano-4-fluoro-3-phenoxy-benzyl alcohol, α-cyano-3-phenoxy-benzyl alcohol, 6-phenoxy-pyrid-2-yl-methanol, 6-phenoxy-pyridine-2-carbaldehyde and α-cyano-6-phenoxy-pyrid-2-yl-methanol.

Preferred substituted 2,2-dimethyl-3-phenyl-cyclopropanecarboxylic acid esters of formula (IV) to be employed as intermediate products, are those in which $R^1$ and $R^2$ have the same meanings as those given in the definition of the corresponding groups prefered and very particularly preferred compounds of formula (I), and $R^6$ represents a methyl or ethyl radical.

The following may be mentioned as examples of the compounds of the formula (IV): methyl 3-(3-bromo-4-trifluoromethoxy-phenyl)-2,2-dimethyl-cyclopropanecarboxylate, methyl 3-(4-trifluoromethoxyphenyl)-2,2-dimethyl-cyclopropanecarboxylate, methyl 3-(4-trifluoromethylthiophenyl)-2,2-dimethyl-cyclopropanecarboxylate, methyl 3-(3-chloro-4-trifluoromethoxy-phenyl)-2,2-dimethyl-cyclopropanecarboxylate, methyl 3-(3,4-trifluoroethylenedioxyphenyl)-2,2-dimethyl-cyclopropanecarboxylate, methyl 3-(3,4-difluoromethylenedioxy-phenyl)-2,2-dimethyl-cyclopropanecarboxylate, methyl 3-(3-chloro-4-(2-chloro-1,1,2-trifluoroethoxy)-phenyl)-2,2-dimethyl-cyclopropanecarboxylate, methyl 3-(3-chloro-4-(1,1,2,2-tetrafluoroethoxy)-phenyl)-2,2-dimethyl-cyclopropanecarboxylate, methyl 3-(3-chloro-4-chlorodifluoromethoxy-phenyl)-2,2-dimethyl-cyclopropanecarboxylate and methyl 3-(3-chloro-4-difluoromethoxy-phenyl)-2,2-dimethyl-cyclopropanecarboxylate, and the corresponding ethyl esters.

The new substituted 2,2-dimethyl-3-phenyl-cyclopropanecarboxylic acid esters of the formula (IV) are obtained according to the process which forms a further subject of the present invention, described previously, by reacting a substituted 2-methyl-3-phenyl-propene of the formula (V) with a diazoacetic acid ester of the formula (VI), in the presence of a catalyst.

Suitable catalysts are copper and copper compounds of various oxidation stages—also mixtures—, such as copper (as a powder or bronze), copper (I) and copper (II) chloride, copper (I) and copper (II) oxide and copper (II) sulphate. The reaction temperature can be varied within a relatively wide range. In general, the reaction is carried out at a temperature between 50° and 200° C., preferably between 80° and 150° C.

Generally, after the end of the evolution of nitrogen, the reaction mixture is cooled, diluted with a water-immiscible solvent (such as methylene chloride) and filtered. The filtrate is washed with water, dried, and worked up by distillation.

Preferred substituted 2-methyl-3-phenyl-propanes of formula (V) to be used as intermediate products are those, in which $R^1$ and $R^2$ have the same meanings as those given in the definition of the corresponding groups in preferred and very particularly preferred compounds of formula (I).

The following may be mentioned as examples of compounds of formula (V): 3-(3-bromo-4-trifluoromethoxy-phenyl)-, 3-(4-trifluoromethoxy-phenyl)-, 3-(4-trifluoromethylthio-phenyl)-, 3-(3-chloro-4-trifluoromethoxy-phenyl)-, 3-(3,4-trifluoroethylenedioxy-phenyl)-, 3-(3,4-difluoromethylenedioxyphenyl)-, 3-(3-chloro-4-(2-chloro-1,1,2-trifluoroethoxy)-phenyl)-, 3-(3-chloro-4-(1,1,2,2-tetrafluoroethoxy)-phenyl)-, 3-(3-chloro-4-chlorodifluoromethoxy-phenyl)- and 3-(3-chloro-4-difluoromethoxy-phenyl)-2-methyl-1-propene.

Diazoacetic acid esters of the formula (VI) are compounds which are known from the literature, and they can be prepared analogously to known processes. The following may be mentioned as examples: methyl diazoacetate and ethyl diazoacetate.

The new substituted 2-methyl-3-phenyl-propenes of the formula (V) are obtained by the process which forms a further subject of the present invention, described previously. This process is carried out according to the methods customary in Wittig conversions of carbonyl to olefin.

The preparation of the phosphorane (VIII) is known.

Some of the substituted benzaldehydes of formula (VII) to be used as intermediate products are known (see, for example, J.Gen.Che. USSR 30 (1960), 3103; Bull.Soc.Chim. France 1955, 1594 ibid. 1962, 254–262; J.Org.Chem. 37 (1972), 673: German Published Specification DOS No. 2,029,556; U.S. Pat. No. 3,387,037; and J. Med.Chem. 16 (1973), 1399).

New benzaldehydes of formula (VII) are those in which $R^1$ has the same meaning as that given in the definition of the corresponding groups in preferred and very particular preferred compounds of formula (I), and $R^2$ represents bromine.

The following may be mentioned as examples of benzaldehydes of formula (VII): 3-bromo-4-trifluoromethoxy-, 4-trifluoromethoxy-, 4-trifluoromethylthio-, 3-chloro-4-trifluoromethoxy-, 3,4-trifluoroethylenedioxy-, 3,4-difluoromethylenedioxy-, 3-chloro-4-(1,1,2,2-tetrafluoroethoxy)-, 3-chloro-4-(2-chloro-1,1,2-trifluoroethoxy)-, 3-chloro-4-chlorodifluoromethoxy- and 3-chloro-4-difluoromethoxy-benzaldehyde.

The new substituted benzaldehydes of the formula (VII) are obtained by the process which forms a further subject of the present invention, described previously. This process for the preparation of compounds of the formula VII (above) is preferably carried out using a diluent. Suitable diluents, if required, are water and/or aliphatic or aromatic, optionally halogenated hydrocarbons (such as pentane, hexane, heptane, cyclohexane, petroleum ether, petrol, ligroin, benzene, toluene, xylene, methylene chloride, ethylene chloride, chloroform, carbon tetrachloride, chlorobenzene and O-dichlorobenzene).

The reaction temperature is generally a temperature between 0° and 100° C., preferably between 10° and 60° C. The process is usually carried out under normal pressure.

In a preferred variant ($\alpha$) for the production of benzaldehydes of formula (VII), chromium (VI) oxide/pyridine/hydrogen chloride (1/1/1) is used as the oxidizing agent. The mixture is worked up by distillation, if appropriate after decantation from undissolved components.

In a second preferred variant ($\beta$) for the production of benzaldehydes of formula (VII), nitric acid is used as the oxidizing agent and water is used as the diluent. For working-up, the mixture is rendered alkaline with sodium hydroxide solution and extracted with a water-immiscible solvent (such as toluene) and the extract is washed with water, dried and filtered, and the filtrate is distilled.

In a third preferred variant ($\gamma$) for the production of benzaldehydes of formula (VII), chromic acid or a dichromate and sulphuric acid are used as the oxidizing agent. The diluent in this case is preferably a two-phase system comprising water and one of the immediately abovementioned organic solvents. Compounds which are suitable for transferring anions from water to organic solvents are preferably used as catalysts. Examples of these are benzyl-triethyl-ammonium bisulphate, tetrabutyl-ammonium bromide and methyl-tricaprylammonium chloride ("Aliquat" 336).

For working-up, the mixture is generally diluted with water, the organic phase is separated off, washed with water, dried and filtered, and the filtrate is distilled.

Preferred substituted benzenes of formula (IX) to be employed as intermediate products are those in which $R^1$ and $R^2$ have the same meanings as those given in the definition of the corresponding groups in the preferred and very particularly preferred compounds of formula (I), and $R^7$ represents a hydroxymethyl group.

The following may be mentioned as examples of compounds of the formula (IX): 3-bromo-4-trifluoromethoxy-, 4-trifluoromethoxy-, 4-trifluoromethylthio-, 3-chloro-4-trifluoromethoxy-, 3,4-trifluoroethylenedioxy-, 3,4-difluoromethylenedioxy-, 3-chloro-4-(2-chloro-1,1,2-trifluoroethoxy)-, 3-chloro-4-(1,1,2,2-tetrafluoroethoxy)-, 3-chloro-4-chlorodifluoromethoxy- and 3-chloro-4-difluoromethoxy-1-hydroxymethyl-benzene.

Benzenes of the formula (IX) are known, and they can be prepared in a known manner (see German Published Specification DOS No. 2,333,849).

They are obtained, for example, by reducing the corresponding carboxylic acid-halide (for example the fluorides) in the presence of sodium boranate and in the presence of a diluent (such as dioxane) at temperatures between 20° and 150° C. (see, also, the preparative examples).

The introduction of the halogen atoms, for example the bromine atoms, into the benzene nucleus of the carboxylic acid-halides used for the reduction described above is effected according to known methods (see Houben-Weyl, Methoden der organischen Chemie (Methods of Organic Chemistry), Volume 5/3, page 215), for example by diazotizing the corresponding aminobenzoic acids in a solution of hydrobromic acid, and then boiling down the mixture. The carboxylic acids are then converted into the corresponding carboxylic acid-halides (see, also, the preparative examples).

The active compounds are well tolerated by plants, have a favorable level of toxicity to warm-blooded animals, and can be used for combating arthropod pests, especially insects, arachnida and nematodes which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example *Reticulitermes* spp.;

from the order of the Anoplura, for example *Phylloxera vastatrix, Pemphigus* spp., *Pediculus humanus corporis, Haematopinus* spp. and *Linognathus* spp.;

from the order of the Mallophaga, for example *Trichodectes* spp. and *Damalinea* spp.;

from the order of the Thysanoptera, for example *Hercinothrips femoralis* and *Thrips tabaci;* from the order of the Heteroptera, for example *Eurygaster* spp., *Dysdercus intermedius, Piesma quadrata, Cimex lectularius, Rhodnium prolixus* and *Triatoma* spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.;

from the order of the Lepidoptera, for example *Pectinophora gossypiella, Bupalus piniarius, Cheimatobia brumta, Lithocolletis blancardella, Huponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the Hymenoptera, for example *Diprion* spp., *Hoplocampa* spp., *Lasius* spp., *Monomorium pharaonis* and *Vespa* spp.;

from the order of the Diptera, for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the Siphonaptera, for example *Xenopsylla cheopis* and *Ceratophyllus* spp.;

from the class of the Arachnida, for example *Scorpio maurus L* and *Latrodectus mactans;* from the order of the Acarina, for example *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp.

The plant-parasitic nematodes include *Pratylenchus* spp., *Radopholus similis, Ditylenchus dipsaci, Tylenchulus semipenetrans, Heterodera* spp., *Meloidogyne* spp., *Aphelenchoides* spp., *Longidorus* spp., *Xiphinema* spp., and *Trichodorus* spp.

The active compounds can be converted into the customary formulations, such as solutions, emulsions, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, wuch as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against pests harmful to health and pests of stored products, the active compounds are distinguished by an excellent residual action on wood and clay as well as a good stability to alkali on limed substrates.

The active compounds according to the invention are also suitable for combating actoparasites and endoparasites in the field of veterinary medicine.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular insects, acarids or nematodes) which comprises applying to the pests, or to a habitat thereof, a compound of the present invention alone or in the form of a composition containing as active ingredient a compound of the present invention in admixture with a diluent or carrier.

The present invention also provides a method of freeing or protecting domesticated animals from parasites which comprises applying to said animals a compound according to the present invention, in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasites by the application to said animals of a compound according to the present invention, in admixture with a diluent or carrier.

The active compounds according to the invention may be used in a known manner in the veterinary sector, such as by oral administration, for example in the form of tablets, capsules, drinks and granules, by dermal application, for example by means of dipping, spraying, pouring on and spotting on, and dusting, and by parenteral administration, for example by means of an injection.

PREPARATIVE EXAMPLES

Example 1

(a) 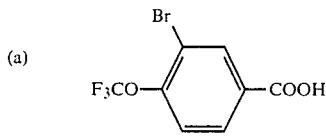

44 g of 3-amino-4-trifluoromethoxybenzoic acid were stirred into a mixture of 440 ml of water and 220 ml of a 48% strength hydrobromic acid solution, and the mixture was diazotized with 14 g of sodium nitrite in 40 ml of water, at 0° to 3° C. The mixture was stirred for a further 15 minutes, and the excess of nitrite was destroyed with amidosulphonic acid. The mixture was then diluted with 300 ml of ice water. This diazo solution was allowed to run into a freshly prepared solution of 10 g of copper (I) bromide in 200 ml of a 48% strength hydrobromic acid solution, at 20° C. The resulting crystals were filtered off under suction and dried. After recrystallization from chlorobenzene, 3-bromo-4-trifluoromethoxybenzoic acid of melting point 124° to 125° C. was obtained.

(b) 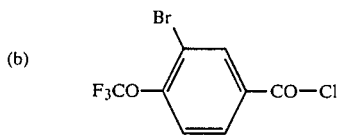

462 g of 3-bromo-4-trifluoromethoxybenzoic acid and 358 ml of thionyl chloride were initially introduced together into the reaction vessel, and were heated up to 70° C., according to the evolution of gas. The mixture was stirred until the evolution of gas had ceased, and the excess thionyl chloride was distilled off under normal pressure. The residue was distilled. The 3-bromo-4-trifluoromethoxybenzoic acid-chloride boiled at 111° C./20 mm Hg and had a refractive index of $n_D^{20}$: 1.5120.

(c) 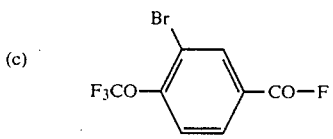

100 ml of anhydrous hydrofluoric acid were cooled to −10° C. 420 g of 3-bromo-4-trifluoromethoxy-benzoyl chloride were added dropwise in the course of two hours at −5° to 0° C., with vigorous evolution of hydrogen chloride. After the evolution of hydrogen chloride had ceased, the temperature was allowed to increase and the reaction allowed to go to completion at 20° C. The excess hydrofluoric acid was distilled off. The residue was purified by distillation. 352.8 g (88.7% of theory) of 3-bromo-4-trifluoromethoxybenzoyl fluoride of refractive index $n_D^{20}$: 1.4760 were obtained.

(d) 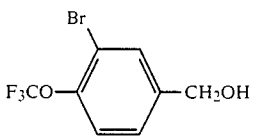

764 ml of dioxane and 53 g of sodium boranate were initially introduced into the reaction vessel, and 400 g of 3-bromo-4-trifluoromethoxybenzoyl fluoride in 364 ml of dioxane were added dropwise in the course of 11 hours, at the reflux temperature. The mixture was further stirred for 1 hour at the reflux temperature. The mixture was cooled and introduced onto ice water. The mixture was acidified with hydrochloric acid, and the organic portion was taken up in methylene chloride. The aqueous layer was extracted twice with methylene chloride, and the combined organic phases were dried over sodium sulphate. They were then distilled. The desired product, 3-bromo-4-trifluoromethoxybenzyl alcohol, had a boiling point of 132° C./20 mm Hg and a melting point of 57° to 58° C.

(e) 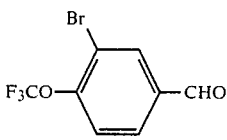 (VII a)

A mixture of 29.4 g (0.3 mol) of sulphuric acid, 50 ml of water and 2 ml of "Aliquat" 336 (tricaprylmethylammonium chloride) was added to a solution of 27 g (0.1 mol) of 3-bromo-4-trifluoromethoxybenzyl alcohol in 250 ml of methylene chloride at room temperature. Thereafter, 9.7 g (0.033 mol) of potassium dichromate were added to the reaction mixture, and the temperature was kept at approx. 25° C. for 2 hours by slight cooling. After 100 ml of water had been added to the mixture, the organic phase was separated off and the water was once again extracted by shaking with 100 ml of methylene chloride. The organic phases were washed twice with 100 ml of water, then once with 100 ml of saturated sodium bicarbonate solution, and once again with 100 ml of water, dried over sodium sulphate, and concentrated by evaporation in vacuo. The residue was distilled. In this manner, 20.4 g (75.8% of theory) of 3-bromo-4-trifluoromethoxybenzaldehyde were obtained as a colorless oil of boiling point 97° C./10 mm Hg.

(f) 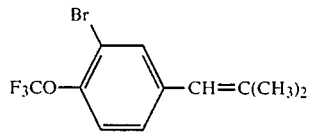 (V a)

150 ml of 20% strength solution of n-butyl-lithium in n-hexane were added dropwise to a suspension of 129.6 g (0.3 mol) of dry isopropyl-triphenylphosphonium iodide in 500 ml of anhydrous tetrahydrofuran, under nitrogen at 0° C. and while stirring. The deep red solution thus obtained was stirred for a further 15 minutes at 0° C., and 80.7 g (0.3 mol) of 3-bromo-4-trifluoromethoxybenzaldehyde were then added dropwise at 0° to 10° C. The mixture was then stirred at room temperature until decolorization occurred (approximately 12 hours). 900 ml of water were then added to the reaction mixture, and the mixture was extracted with 5 times 200 ml of petroleum ether. The petroleum ether phases were dried over magnesium sulphate, and the solvent was then stripped off in a rotary evaporator, in the vacuum from a water jet. 150 ml of n-hexane were added to the residue, and the mixture was stirred thoroughly and then filtered. The solvent was then distilled off from the filtrate under normal pressure, and the oily residue was then distilled in vacuo. 50 g (56.5% of theory) of 1-(3-bromo-4-trifluoromethoxyphenyl)-2-methyl-prop-1-ene were obtained as a slightly yellowish liquid of boiling point 107° to 108° C./10 mm Hg.

The following compounds of the formula (V) were obtained analogously:

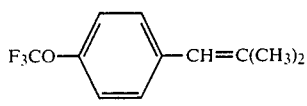

(V b)

Yield: 44% of theory
Bp.: 65–67° C./4 mm Hg

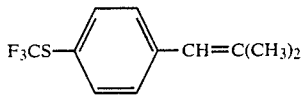

(V c)

Yield: 53% of theory
Bp.: 95–96° C./10 mm Hg (g)

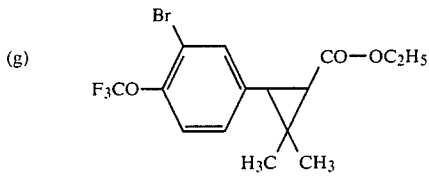

(IV a)

A mixture of 33.3 g (0.11 mol) of 1-(3-bromo-4-trifluoromethoxyphenyl)-2-methyl-prop-1-ene, 1.2 g of copper powder and 0.9 g of copper sulphate (anhydrous) was heated to 120° to 130° C., and a mixture of 16.6 g (0.056 mol) of 1-(3-bromo-4-trifluoromethoxyphenyl)-2-methyl-prop-1-ene and 19.4 g (0.17 mol) of ethyl diazoacetate was then very slowly added dropwise in the course of 6 hours, also at 120° to 130° C., while stirring. After evolution of nitrogen had ceased, the mixture was cooled, diluted with 500 ml of methylene chloride and then filtered. The filtrate was extracted by shaking with 500 ml of water, the organic phase was then separated off and dried over magnesium sulphate, and the solvent was then distilled off in the vacuum from a water jet. The oily residue was distilled in vacuo. In this procedure, two fractions were obtained:
Fraction 1: Boiling point 100° to 110° C./10 mm Hg
Fraction 2: Boiling point 120° to 160° C./10 mm Hg Fraction 1 proved to be unreacted 1-(3-bromo-4-trifluoromethoxyphenyl)-2-methyl-prop-1-ene.

Fraction 2 was distilled again. 8 g (13% of theory) of ethyl (±)-cis/trans-3-(3-bromo-4-trifluoromethoxyphenyl)-2,2-dimethyl-cyclopropanecarboxylate were obtained as a colorless liquid of boiling point 145° to 160° C./10 mm Hg.

The following compounds of the formula (IV) were obtained analogously:

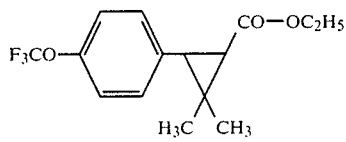

(IV b)

Yield: 19% of theory
Bp.: 115–125° C./3 mm Hg

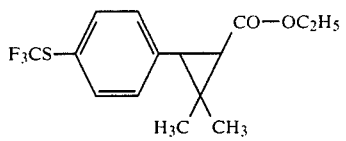

(IV c)

Yield: 20% of theory
Bp.: 125–130° C./5 mm Hg (h)

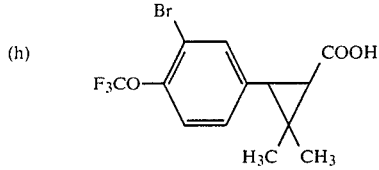

(II-A)

16 g (0.042 mol) of ethyl 3-(3-bromo-4-trifluoromethoxyphenyl)-2,2-dimethyl-cyclopropanecarboxylate were dissolved in 50 ml of ethanol, a solution of 3.4 g (0.085 mol) of sodium hydroxide in 50 ml of water was then added, and the mixture was heated under reflux for 4 hours, while stirring. The ethanol was then distilled off in the vacuum from a water jet, the residue was taken up in 300 ml of water, and the solution was extracted once with 300 ml of methylene chloride. The aqueous phase was separated off, acidified with concentrated hydrochloric acid and then extracted twice with 300 ml of methylene chloride. The organic phase was then separated off and dried over magnesium sulphate, and the solvent was distilled off in the vacuum from a water jet. The last residues of solvent were removed by incipient distillation for a short time, at a bath temperature of 50° C./2 mm Hg. 9.8 g (66.3% of theory) of (±)cis/trans-3-(3-bromo-4-trifluoromethoxyphenyl)-2,2-dimethyl-cyclopropanecarboxylic acid were then obtained as a yellow viscous oil. The structure was confirmed by the $^1$H-NMR spectrum.

The following compounds of the formula (II) were obtained analogously:

(II b)

Yield: 65% of theory

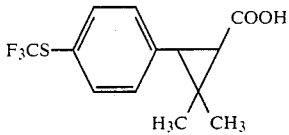

(II c)

19

-continued (i) 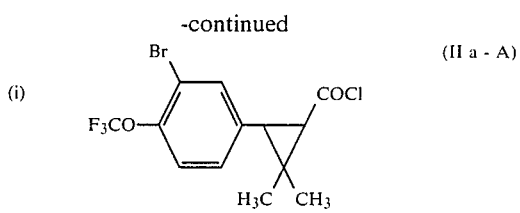

(II a - A)

9.6 g (0.027 mol) of 3-(3-bromo-4-trifluoromethoxy-phenyl)-2,2-dimethyl-cyclopropanecarboxylic acid were dissolved in 100 ml of carbon tetrachloride, and 10 g of thionyl chloride were slowly added dropwise at 60° C., while stirring. The mixture was then heated under reflux for 4 hours. After the reaction period had ended, excess thionyl chloride, as well as carbon tetrachloride, were distilled off in the vacuum from a water jet. 9.4 g (93.7% of theory) of 3-(3-bromo-4-trifluoromethoxy-phenyl)-2,2-dimethyl-cyclopropanecarboxylic acid-chloride were obtained as a yellow liquid.

The remaining acid-chlorides of the formula (IIa) were obtained analogously.

(j) 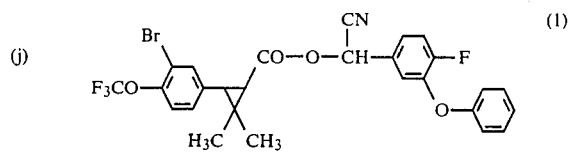

(1)

2.62 g (0.012 mol) of 4-fluoro-3-phenoxy-benzaldehyde and 4.5 g (0.012 mol) of (±)cis/trans-3-(3-bromo-4-trifluoromethoxyphenyl)-2,2-dimethyl-cyclopropanecarboxylic acid-chloride were added together, dropwise, to a mixture of 1.0 g of sodium cyanide, 1.5 ml of water, 50 ml of cyclohexane and 0.3 g of tetrabutylammonium bromide, while stirring at 20° to 25° C., and the mixture was stirred for 4 hours at 20° to 25° C. 300 ml of toluene were then added to the reaction mixture, and the mixture was extracted by shaking twice with 300 ml of water. The organic phase was separated off and dried over magnesium sulphate, and the solvent was distilled off in the vacuum from a water jet. The last residues of solvent were removed by incipient distillation for a short time, at a bath temperature of 60° C./1 mm Hg. 4.0 g (57.7% of theory) of 4-fluoro-3-phenoxy-α-cyano-benzyl (±)cis/trans-3-(3-bromo-4-trifluoromethoxy-phenyl)-2,2-dimethyl-cyclopropanecarboxylate were obtained as a viscous oil.

The structure was confirmed by the $^1$H-NMR spectrum. $^1$H-NMR in COCl$_3$/TMS, τ (ppm):

Aromatic H: 2.5–3.25 (m/11H)

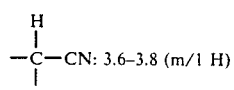

—C—CN: 3.6–3.8 (m/1 H)

Cyclopropane-H: 7.2–8.2 (m/2H)
Dimethyl-H: 8.55–9.15 (m/6H)

20

Example 2

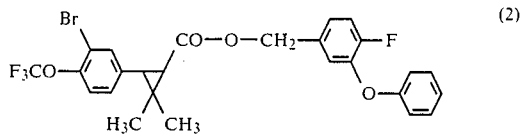

(2)

2.64 g (0.012 mol) of 4-fluoro-3-phenoxy-benzyl alcohol and 4.5 g (0.012 mol) of (±)cis/trans-3-(3-bromo-4-trifluoromethoxy-phenyl)-2,2-dimethyl-cyclopropanecarboxylic acid-chloride were distilled in 100 ml of anhydrous toluene. 1.2 g of pyridine, dissolved in 10 ml of anhydrous toluene, were added dropwise at a temperature of 20° to 25° C., while stirring. The mixture was then stirred for a further 4 hours at 25° to 35° C. The reaction mixture was poured into 150 ml of water to which 10 ml of concentrated hydrochloric acid were added, and the organic phase was separated off and again washed with 100 ml of water. The toluene phase was then dried over sodium sulphate, and the solvent was distilled off in the vacuum from a water jet. The last residues of solvent were removed by incipient distillation for a short time, at a bath temperature of 60° C./1 mm Hg. 5.7 g (85.9% of theory) of 4-fluoro-3-phenoxy-benzyl (±)cis/trans 3-(3-bromo-4-trifluoromethoxy-phenyl)-2,2-dimethyl-cyclopropanecarboxylate were obtained as a yellow oil.

The structure was established by the $^1$H-NMR spectrum. $^1$H-NMR in CDCl$_3$/TMS, τ (ppm):

Aromatic-H: 2.5–3.2 (m/11H)
Benzyl-H: 4.95 (s) and 5.05 (s), 2H in total
Cyclopropane-H: 7.3–8.20 (m/2H)
Dimethyl-H: 8.6–9.15 (m/6H)

The following compounds of the formula (I) could be prepared analogously to Examples 1 and 2:

TABLE 2

| Compound No. | R$^1$ | R$^2$ | R$^3$ | R$^4$ | R$^5$ | Y | $^1$H—NMR in CDCl$_3$/TMS, τ(ppm) |
|---|---|---|---|---|---|---|---|
| 3 | F$_3$CO | H | CN | 4-F | H | CH | H<br>\|<br>—C—CN:<br>\|<br>3.57–3.80 (m/1 H) |
| 4 | F$_3$CO | H | H | 4-F | H | CH | Benzyl-H: 4.88(s) 5.05(s)/2 H |
| 5 | F$_3$CS | H | CN | 4-F | H | CH | |
| 6 | F$_3$CO | Br | CN | H | H | CH | |
| 7 | F$_3$CS | H | H | 4-F | H | CH | |
| 8 | F$_3$CO | Br | H | H | H | CH | |
| 9 | F$_3$CO | Br | H | H | H | N | |

The insecticidal and acaricidal activity of compound of this invention is illustrated by the following biotest examples.

In these examples, the compounds according to the present invention are each identified by the number (given in brackets) from Examples 1 and 2 and Table 2 hereinabove:

Example 3

Phaedon larvae test
Solvent: 3 parts by weight of acetone
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Cabbage leaves (Brassica oleracea) were treated by being dipped into the preparation of the active compound of the desired concentration and were infested with mustard beetle larvae (Phaedon cochleariae), so long as the leaves were still wet.

After the specified periods of time, the destruction in % was determined. 100% meant that all the beetle larvae had been killed; 0% meant that none of the beetle larvae had been killed.

In this test, for example, the following compounds showed a superior activity compared to the prior art: (1), (3) and (4).

Example 4

Tetranychus test (resistant)
Solvent: 3 parts by weight of acetone
Emulsifier: 1 part by weight of alkylaryl polyglycol ether.

To produce a suitable preparation of active compound, 1 part by weight of active compound was mixed with the stated amount of solvent and the stated amount of emulsifier, and the concentrate was diluted with water to the desired concentration.

Bean plants (Phaseolus vulgaris) which were heavily infested with the common spider mite or two-spotted spider mite (Tetranychus urticae) in all stages of development were treated by being dipped into the preparation of the active compound of the desired concentration.

After the specified periods of time, the destruction in % was determined. 100% meant that all the spider mites had been killed; 0% meant that none of the spider mites had been killed.

In this test, for example, the following compound showed a superior activity compared to the prior art: (3)

Example 5

Critical concentration test/soil insects
Test insect: Agrotis segetum larvae (in the soil)
Solvent: 3 parts by weight of acetone
Emulsifier: 1 part by weight of alkylaryl polyglycol ether.

To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l) being decisive. The soil was filled into pots and the pots were left to stand at room temperature.

After 24 hours, the test animals were introduced into the treated soil, and after a further 2 to 7 days the degree of effectiveness of the active compound was determined in % by counting the dead and live test insects. The degree of effectiveness was 100% if all the test insects had been killed and was 0% if just as many test insects were still alive as in the case of the untreated control.

In this test, for example, the following compound showed a superior action compared to the prior art: (3)

Example 6

In vitro immersion test/ectoparasites

Test with Boophilus microplus resistant
Solvent:
 35 parts by weight of ethylene glycol monomethyl ether
 35 parts by weight of nonylphenol polyglycol ether To produce a suitable preparation of active compound, three parts by weight of active compound were mixed with seven parts by weight of the solvent mixture indicated above, and the concentrate thus obtained was diluted with water to the desired concentration.

10 adult Boophilus microplus res. were immersed for 1 minute in the active compound preparation to be tested. After transfer to plastic beakers and storage in a climatically controlled chamber, the degree of destruction was determined.

In this test, for example, the following compounds showed a superior activity compared to the prior art: (4), (3), (1) and (2).

It will be appreciated that the instant specification and examples are set forth by way of illustration and not limitation, and that various modifications and changes may be made without departing from the spirit and scope of the present invention.

We claim:

1. A substituted phenyl-cyclopropanecarboxylic acid ester of the formula

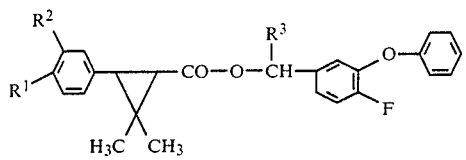

in which
R$^1$ is C$_1$- or C$_2$-fluoroalkoxy, C$_1$- or C$_2$-chlorofluoroalkoxy, C$_1$- or C$_2$-fluoroalkylthio or C$_1$- or C$_2$-chlorofluoroalkylthio,
R$^2$ is H, Cl or Br, and
R$^3$ is H or CN.

2. A compound according to claim 1, wherein such compound is 4-fluoro-3-phenoxy-α-cyano-benzyl 3-(3-bromo-4-trifluoromethoxy-phenyl)-2,2-dimethyl-cyclopropanecarboxylate of the formula

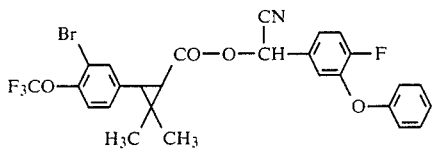

3. A compound according to claim 1, wherein such compound is 4-fluoro-3-phenoxy-benzyl 3-(3-bromo-4- trifluoromethoxy-phenyl)-2,2-dimethyl-cyclopropanecarboxylate of the formula

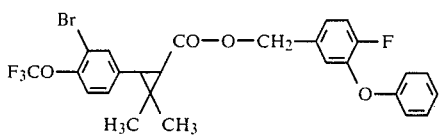

4. A compound according to claim 1, wherein such compound is 4-fluoro-3-phenoxy-α-cyano-benzyl 3-(4-trifluoromethoxy-phenyl)-2,2-dimethyl-cyclopropanecarboxylate of the formula

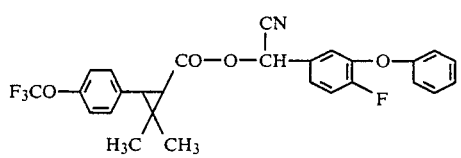

5. A compound according to claim 1, wherein such compound is 4-fluoro-3-phenoxy-benzyl 3-(4-trifluoromethoxyphenyl)-2,2-dimethyl-cyclopropanecarboxylate of the formula

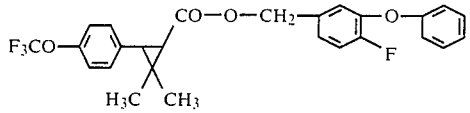

6. A pesticidal composition comprising a pesticidally effective amount of a compound according to claim 1 in admixture with a diluent.

7. A method of combating pests comprising applying to the pests, or to a habitat thereof, a pesticidally effective amount of a compound according to claim 1.

8. The method according to claim 7, wherein such compound is
4-fluoro-3-phenoxy-α-cyano-benzyl 3-(3-bromo-4-trifluoromethoxy-phenyl)-2,2-dimethyl-cyclopropanecarboxylate,
4-fluoro-3-phenoxy-benzyl 3-(3-bromo-4-trifluoromethoxy-phenyl)-2,2-dimethyl-cyclopropanecarboxylate,
4-fluoro-3-phenoxy-α-cyano-benzyl 3-(4-trifluoromethoxy-phenyl)-2,2-dimethyl-cyclopropanecarboxylate, or
4-fluoro-3-phenoxy-benzyl 3-(4-trifluoromethoxy-phenyl)-2,2-dimethyl-cyclopropanecarboxylate.

* * * * *